United States Patent
Nelson et al.

(10) Patent No.: US 10,065,171 B2
(45) Date of Patent: Sep. 4, 2018

(54) SYSTEM AND PROCESS FOR CUMENE HYDROPEROXIDE CLEAVAGE WITH IMPROVED ONLINE INSTRUMENTATION CONFIGURATION

(71) Applicant: SABIC Global Technologies B.V., Bergen op Zoom (NL)

(72) Inventors: Mark Erik Nelson, Mt. Vernon, IN (US); James Patrick Williams, Grayville, IL (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/520,559

(22) PCT Filed: Oct. 22, 2015

(86) PCT No.: PCT/US2015/056799
§ 371 (c)(1),
(2) Date: Apr. 20, 2017

(87) PCT Pub. No.: WO2016/065093
PCT Pub. Date: Apr. 28, 2016

(65) Prior Publication Data
US 2017/0304798 A1    Oct. 26, 2017

Related U.S. Application Data

(60) Provisional application No. 62/068,112, filed on Oct. 24, 2014.

(51) Int. Cl.
| | |
|---|---|
| *C07C 45/53* | (2006.01) |
| *C07C 37/08* | (2006.01) |
| *C07C 407/00* | (2006.01) |
| *B01J 19/00* | (2006.01) |
| *B01J 19/24* | (2006.01) |

(52) U.S. Cl.
CPC ......... *B01J 19/2465* (2013.01); *B01J 19/242* (2013.01); *B01J 19/245* (2013.01); *C07C 37/08* (2013.01); *C07C 45/53* (2013.01); *C07C 407/00* (2013.01); *B01J 2219/00006* (2013.01); *B01J 2219/00087* (2013.01)

(58) Field of Classification Search
CPC ....... C07C 45/53; C07C 37/08; C07C 407/00; B01J 19/2465
USPC .................................................. 568/385, 798
See application file for complete search history.

(56) References Cited

U.S. PATENT DOCUMENTS

| | | |
|---|---|---|
| 2,989,517 A | 6/1961 | Hanson et al. |
| 6,057,483 A | 5/2000 | Zakoshansky et al. |

FOREIGN PATENT DOCUMENTS

| | | |
|---|---|---|
| WO | 03100395 A1 | 12/2003 |
| WO | 2004074230 A1 | 9/2004 |

OTHER PUBLICATIONS

International Search Report for International Application No. PCT/US2015/056799; dated Feb. 10, 2016; 5 pages.
Written Opinion of the International Search Report for International Application No. PCT/US2015/056799; dated Feb. 10, 2016; 7 pages.

*Primary Examiner* — Sikarl A Whitherspoon
(74) *Attorney, Agent, or Firm* — Cantor Colburn LLP

(57) ABSTRACT

Disclosed herein are a method and systems for cumene hydroperoxide cleavage with an improved configuration for online instrumentation. The systems comprise a first fluid loop comprising one or more reactors and a fluid pump and a second fluid loop in fluid communication with the first fluid loop. This second fluid loop comprises an instrument configured to measure a characteristic of a fluid flowing through the second loop, wherein an input of the second fluid loop is disposed downstream of said fluid pump and an output of the second fluid loop is disposed upstream of said fluid pump. The method comprises causing fluid to flow within a first stage comprising one or more reactors and a fluid pump, wherein the first stage is configured to decompose a cumene hydroperoxide in the presence of a catalyst mixture to form a dicumyl peroxide mixture. The method also comprises causing at least a portion of the fluid to flow through a instrumentation line in open fluid communication with the first stage. This instrumentation line comprises an instrument configured to measure a characteristic of the fluid flowing through the instrumentation line and an input of the instrument line is disposed downstream of said fluid pump.

17 Claims, 2 Drawing Sheets

SYSTEM AND PROCESS FOR CUMENE HYDROPEROXIDE CLEAVAGE WITH IMPROVED ONLINE INSTRUMENTATION CONFIGURATION

CROSS REFERENCE TO RELATED APPLICATIONS

This application is a 371 of International Application No. PCT/US2015/056799, filed Oct. 22, 2015, which claims priority to U.S. Application No. 62/068,112 filed Oct. 24, 2014, both of which are incorporated herein by reference in their entirety.

FIELD OF DISCLOSURE

The present disclosure relates to cumene hydroperoxide (CHP) cleavage. More specifically, the disclosure relates to processes and system configurations for online instrumentation of systems such as a process system for cumene hydroperoxide cleavage.

BACKGROUND

Cumene is commonly utilized for the production of phenol and acetone. Such production involves the generation of cumene oxidation products cumene hydroperoxide (CHP) and dimethyl benzyl alcohol (DMBA). Reactive peroxide CHP decomposes and dicumyl peroxide (DCP) is produced from DMBA and CHP. The addition of acetone provides a mixture containing the desired phenol and acetone, as well as dimethyl benzyl alcohol (DMBA) and dicumyl peroxide (DCP). Flow reactor systems designed to carry out the cleavage and maximize the reaction output are also commonly plagued with inefficiencies. In a given cleavage system, cumene levels can be diminished where there are upset conditions or valve malfunctions. This can ultimately diminish the yield of cumene hydroperoxide cleavage.

Moreover, currently used reactor systems often employ cumbersome means for monitoring reaction conditions, effectively reducing system efficiency. Traditional online quantitative measurement devices can be configured into cleavage reaction systems to assess the water and organic composition of the reaction stream. These standard devices often require filters which must be regularly changed as they frequently become obstructed. Often, the sample for assessment must be diverted from the reaction flow, thereby depleting the reactant. Thus, there remains a need for a reaction system configuration that can reduce or eliminate cumene depletion and ultimately improve the overall robustness of the cleavage system. Furthermore, there is also a need in the art for a system configuration that incorporates a more efficient and accurate online assessment protocol. This need and other needs are addressed by the present disclosure.

SUMMARY OF THE DISCLOSURE

As described in more detail herein, the present disclosure provides processes, apparatuses, and systems for online instrumentation configurations for a system such as a process system configured for cumene hydroperoxide cleavage.

In an aspect, one system can comprise a first fluid loop comprising one or more reactors and a fluid pump configured in fluid communication with each other. As an example, the fluid pump can be configured to cause an output of the one or more reactors to flow as an input to the one or more reactors. A second fluid loop can be in fluid communication with the first fluid loop, the second fluid loop comprising an instrument configured to measure characteristics of a fluid flowing through the second loop. As a further example, an input of the second fluid loop can be disposed downstream of the fluid pump and an output of the second fluid loop is disposed upstream of the fluid pump.

In another aspect, the disclosure relates to a cumene hydroperoxide cleavage system comprising online instrumentation such as a near-infrared spectroscopy probe.

In an aspect, one system can comprise a first stage including one or more reactors and a fluid pump configured in fluid communication with each other. The fluid pump can be configured to cause an output of the one or more reactors to flow as an input to the one or more reactors. The first stage can be configured to decompose a cumene hydroperoxide in the presence of a catalyst mixture to form a dicumyl peroxide mixture. An instrumentation line can be in open fluid communication with the first stage. The instrumentation line can comprise an instrument configured to measure characteristics of a fluid flowing through the instrumentation line. An input of the instrumentation line can be disposed downstream of the fluid pump.

In one aspect, the disclosure relates to a process comprising the steps of: causing fluid to flow within a first stage in fluid communication with a fluid pump and causing at least a portion of the fluid to flow through an instrumentation line in open fluid communication with the first stage.

BRIEF DESCRIPTION OF THE FIGURES

The accompanying figures, which are incorporated in and constitute a part of this specification, illustrate several aspects and together with the description serve to explain the principles of the disclosure.

Figure 1:
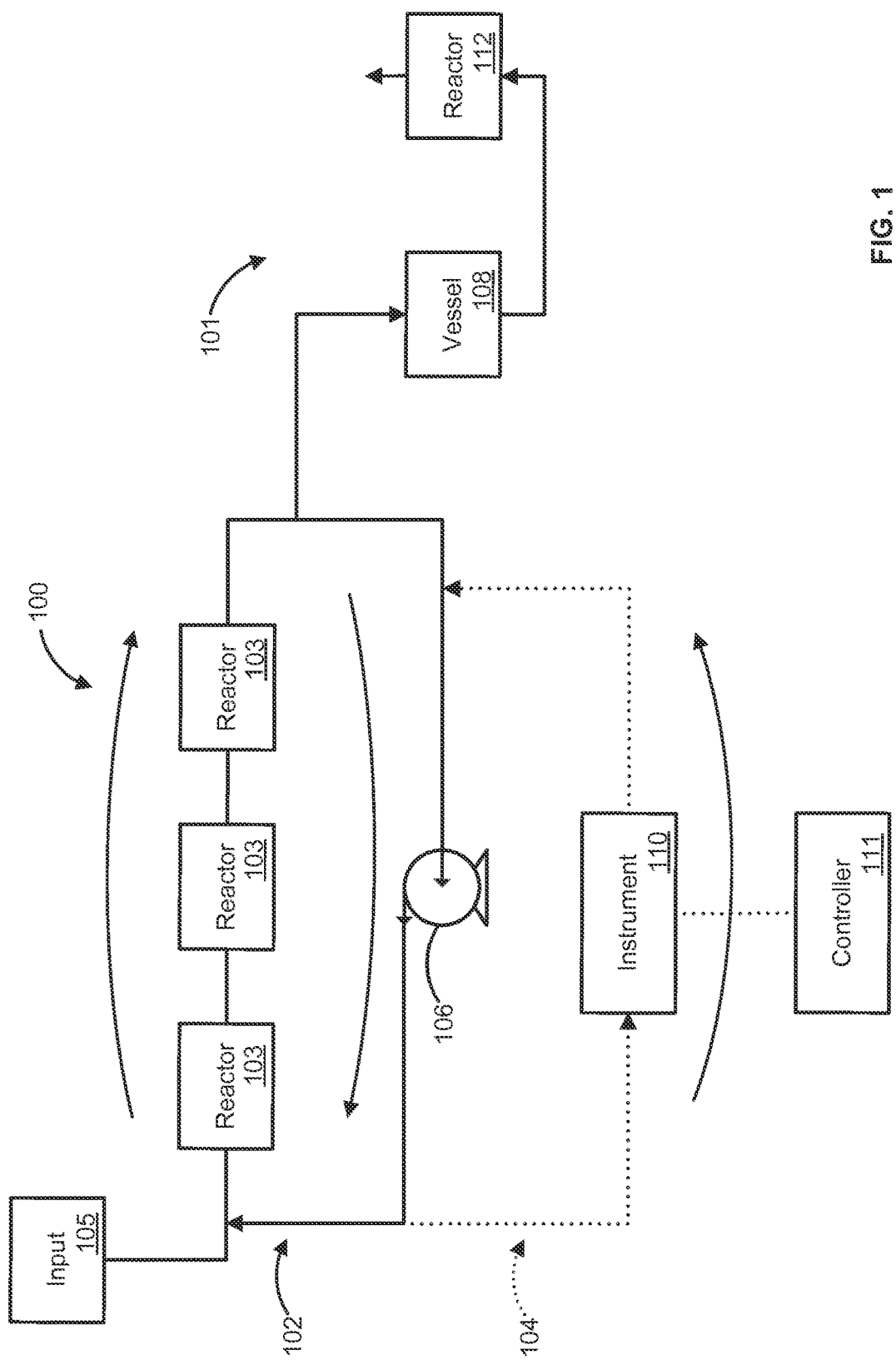
FIG. 1 shows a schematic of a system for converting cumene to phenol and acetone.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

The present disclosure can be understood more readily by reference to the following detailed description of the disclosure and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present disclosure, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present disclosure is not entitled to antedate such publication by virtue of prior disclosure. Further, the dates of publication provided herein may be different from the actual publication dates, which can require independent confirmation.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, example methods and materials are now described.

As used in the specification and the appended claims, the singular forms "a," "an" and "the" include plural referents unless the context clearly dictates otherwise. Thus, for example, reference to "a ketone" includes mixtures of two or more ketones.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent 'about,' it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not. For example, the phrase "optionally substituted alkyl" means that the alkyl group can or cannot be substituted and that the description includes both substituted and un-substituted alkyl groups.

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the disclosure. Thus, if there are a variety of additional steps that can be performed it is understood that each of these additional steps can be performed with any specific aspect or combination of aspects of the methods of the disclosure.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included. For example if a particular element or component in a composition or article is said to have 8% weight, it is understood that this percentage is relation to a total compositional percentage of 100%.

As used herein, "open fluid communication" refers to the absence of a valve or valve-like component at any given interface in the system. For example, in some embodiments, the first fluid loop and the second fluid loop are in open fluid communication. Accordingly, at the interface between the first fluid loop and the second fluid loop (or instrumentation line), there is no valve. The configuration results in reduced equipment, reduced piping, reduced control logic code, and the measurement of all variables in either start-up/shut down or normal operation.

In the context of this disclosure, "minimized" means reduced to the smallest degree possible. For example, in some embodiments, the chemical and physical interactions are less than 20%, 10% or 5% of that found with an uncoated surface. The term "high throughput" is typically associated with a system where at least 80% yield is accomplished at steady state.

Each of the materials disclosed herein are either commercially available and/or the methods for the production thereof are known to those of skill in the art.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Systems

In an aspect, the disclosure concerns systems comprising one or more reactors. As an example, the systems can be used for a high throughput method of formation of phenol and acetone from a cumene hydroperoxide mixture. In further aspects, a cumene hydroperoxide is first decomposed and a feed stream of a resulting cumene oxidation product and a converted oxidation product passes into a reactor (or one or more reactors). An acid catalyst in these reactors decomposes the remaining CHP and the formed DCP to an output product comprising phenol, acetone, and alpha-methylstyrene (AMS), and other by-products.

In some aspects, cumene hydroperoxide cleavage takes place in a two stage system. In an aspect, the system can comprise a first stage 100 and a second stage 101. In the first stage 100, comprising one or more reactors 103, cumene hydroperoxide can be decomposed in the presence of a catalyst mixture to form a mixture of phenol and acetone. At the same time, a portion of the CHP can be reacted with DMBA to form dicumyl peroxide (DCP). In the second stage 101, the product of the first stage 100 can be fed to one or more reactors 112 (or systems, such as a purification system) to form a phenol, acetone, and AMS mixture, for example, from decomposition of the dicumyl peroxide mixture formed in the first stage 100. Other stages, sequences, and processing can be used.

In an aspect, the first stage 100 of a system (e.g., cumene hydroperoxide cleavage system) can comprise a first fluid loop 102. The first fluid loop 102 can comprise conduits, vessels, reactors, and the like forming loop of fluid flow, wherein at least a portion of a fluid is returned upstream in the fluid flow. The first fluid loop 102 can comprise tubing, a heat exchanger, a calorimeter, or any combination thereof. The first fluid loop 102 can comprise one or more reactors 103.

In some aspects, the first fluid loop 102 can be configured to decompose a cumene hydroperoxide received from an input 105. As an example, the first fluid loop 102 can be configured to decompose a cumene hydroperoxide in the presence of a catalyst mixture. In another example, the first fluid loop 102 can be configured both to decompose a cumene hydroperoxide in the presence of a catalyst mixture to form acetone and phenol and to react CHP with DMBA to form dicumyl peroxide. In a further aspect, the second stage 101 can be configured to decompose the remaining CHP and formed dicumyl peroxide, which can be received from the first fluid loop 102, to form a phenol, acetone, and AMS mixture.

In an aspect, the first fluid loop 102 can comprise a fluid pump 106. The first fluid loop 102 and fluid pump 106 can be in fluid communication with each other. The fluid pump 106 can be configured to cause an output of the one or more reactors 103 to flow as an input to the one or more reactors 103. In a further aspect, the system can comprise a vessel 108. The vessel 108 can be in fluid communication with the output of the one or more reactors 103 to receive a fluid therefrom. The vessel 108 can be storage vessel, a pre-heater, a reactor, a processing tank, and the like.

In a further aspect, the first stage 100 of the system can comprise a second fluid loop 104. The second fluid loop 104 can comprise conduits, vessels, reactors, and the like forming loop of fluid flow, wherein at least a portion of a fluid is returned upstream in the fluid flow. As an example, the second fluid loop 104 can be in fluid communication with the first fluid loop 102.

In an aspect, the second fluid loop 104 can be in open fluid communication with the first fluid loop 102. In a further aspect, the second fluid loop 104 can comprise an instrument 110 configured to measure characteristics of a fluid flowing through the second fluid loop 104. In an aspect, the instrument 110 can be configured to measure one or more of water percentage, conductivity, flow rate, and spectral characteristics (e.g., NIR spectroscopy characteristics). The instrument 110 can be configured to measure a variety of characteristics of a fluid flowing in the second fluid loop 104. As an example, the instrument 110 can be an on-line instrument configured to measure real-time characteristics. In a further aspect, an input of the second fluid loop 104 can be disposed downstream of the fluid pump 106. In other aspects, an output of the second fluid loop 104 can be disposed upstream of the fluid pump 106.

Reactors

In one aspect, one or more systems comprise a reactor (e.g., reactor 103, reactor 112). In an aspect, the reactor can comprise a vessel. In a further aspect, the reactor can comprise a reaction chamber. In a still further aspect, the reactor can comprise a conduit.

Figure 2:
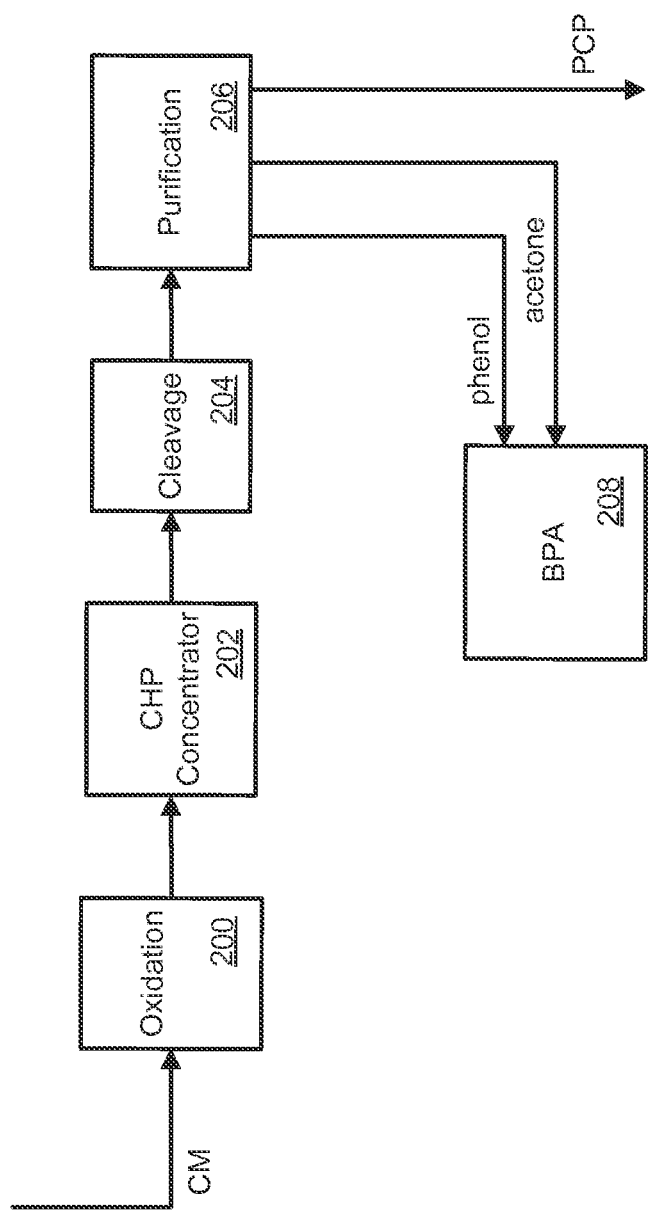
FIG. 2 shows a schematic of a system for converting cumene to phenol and acetone and ultimately to bisphenol A.

In certain aspects of the present disclosure, as illustrated in FIG. 2, cumene is fed to an oxidation reactor 200 to produce a cumene oxidation product comprising cumene hydroperoxide (CHP) and a significant side-product dimethyl benzyl alcohol (DMBA). The cumene oxidation product is optionally fed to a CHP concentrator 202 to increase the concentration of CHP. The product of the oxidation reactor or the concentrator may be fed to the CHP cleavage reactor 204 where CHP is converted to a mixture comprising one or more of phenol, acetone and alpha-methylstyrene (which may be converted to paracumylphenol (PCP)). The product of the CHP cleavage rector may be purified (purifier 206) to isolate acetone and phenol. The acetone and phenol can then be fed to a Bisphenol-A (BPA) reactor 208 to produce BPA product.

A. Oxidation Reactor

In the first step of the cumene-to-phenol process, the cumene feed can enter an oxidation reactor. In one aspect, the oxidation reactor is configured to receive a cumene feed and an oxidizing agent. In another aspect, the oxidation reactor outputs a cumene oxidation product comprising cumene hydroperoxide and dimethyl benzyl alcohol.

The oxidation reactor can circulate the cumene flow through a cascade of large bubble columns. In the bubble columns, the air is added at the bottom of each reactor and the oxygen can transfer from the air bubbles into the cumene. The oxidation reaction can be auto-catalyzed by the cumene hydroperoxide. The oxidation reactor can operate at pressures ranging from atmospheric to around 700 kPa. The temperature of the oxidation reactor can range from 80° C.-120° C. The residence for a single reactor can range from 30 minutes to several hours. In an aspect, the system can comprise multiple oxidation reactors in series. For example, the system can comprise three or four oxidation reactors in series. In another example, the system can comprise six or seven oxidation reactors in series.

The cumene feed can be produced, for example, from benzene and propylene. In one aspect, the cumene is produced commercially using a heterogeneous zeolite catalyst or an acid catalyst, for example, phosphoric acid and aluminum chloride.

The oxidizing agent can be any agent capable of oxidizing the cumene. In one aspect, the oxidizing agent is oxygen. The oxygen can be pure or as a mixture with other gases, for example the mixture of gases found in air. In another aspect, the oxidizing agent is air.

The cumene oxidation product comprises cumene hydroperoxide. The oxidation reactor can also output one or more by-products. The one or more by-products can include acetophenone (ACP) or methyl hydroperoxide (MHP), dimethyl benzyl alcohol, or a combination thereof.

In one aspect, the cumene oxidation product comprises from about 20 weight percent to about 30 weight percent cumene hydroperoxide and from about 2 weight percent to about 3 weight percent dimethyl benzyl alcohol.

B. Stripping Element

In an aspect, the system can optionally further comprise a stripping element (or CHP concentrator) in communication with the oxidation reactor, the stripping element configured to receive the cumene oxidation product and to modify a concentration of the cumene oxidation product, wherein the conversion reactor is configured to receive the modified cumene oxidation product. Typically the concentration of CHP would be increased in this element.

C. Conversion Reactor

In some aspects, the optional conversion reactor (or DMBA reactor) may be configured to receive the cumene oxidation product and to convert at least a portion of the dimethyl benzyl alcohol to cumene hydroperoxide by reacting the at least a portion of the dimethyl benzyl alcohol with hydrogen peroxide. In some aspects, the converted cumene oxidation product comprises from about 20 weight percent to about 32 weight percent cumene hydroperoxide and from about 0.1 weight percent to about 0.7 weight percent dimethyl benzyl alcohol. In some aspects, the converted cumene oxidation product comprises from about 20 weight percent to about 32 weight percent cumene hydroperoxide and from about 0.1 weight percent to about 0.7 weight percent dimethyl benzyl alcohol.

D. Cleavage Reactor

In the system, a feed stream from the conversion reactor (CHP cleavage reactor) of the cumene oxidation product and the converted oxidation product can pass into a cleavage reactor. An acid catalyst in the cleavage reactor can decompose the cumene oxidation product and the converted oxidation product into an output product comprising phenol, acetone, and alpha-methylstyrene, and other by-products.

In some aspects, the cleavage takes place in a two stage system. In a first stage, comprising one or more reactors, cumene hydroperoxide is decomposed in the presence of a catalyst mixture to form a dicumyl peroxide (DCP) mixture along with the desired products acetone and phenol. In a second stage, the product of the first stage can be processed (by one or more reactors or other systems) to form a phenol, acetone, and AMS mixture, for example by decomposition of the dicumyl peroxide mixture formed in the first stage. As described herein, the first and the second stages can be connected in series.

The cleavage reaction can be extremely fast due to it exothermic nature and is essentially to completion in most processes. In one aspect, the cleavage reaction can occur within 30 seconds to 5 minutes. In fact it is common to use a constant boiling or refluxing type system for the isothermal cleavage reaction. This is generally the constant boiling temperature of the cumene oxidation product, the converted oxidation product, and the output product present in the cleavage reactor at a given moment. Generally this can vary from about 70° to 90° C. Since this is the general cumene oxidation product and the converted oxidation product feed stream as well as the output product; the phenol to acetone molar ratio is essentially 1 to 1 throughout the course of the reaction.

The acid catalyst in the cleavage reactor can be any acidic material. To avoid corrosion, heavily corrosive inorganic acids, for example, hydrochloric acid or hydrobromic acid are not usually used in the cleavage reactor. Acid catalysts that can be used include, for example, phosphoric acid or sulfuric acid or a combination thereof. In one aspect, the acid catalyst can be present in the quantity of about 100 to 350 parts per million of sulfuric acid per weight of composition mass.

In some aspects, the cleavage reaction may be run in the presence of excess acetone. In this regard, the addition of recycle acetone may be used in the stream entering the cleavage reactor.

Other by-products that can be formed in the cleavage reactor include, for example, hydroxyacetone, 2-methylbenzofuran, or a combination thereof. The by-products formed in the cleavage reactor can also include some aldehydes, for example, acetaldehyde.

The output product from the cleavage reactor can be cooled. In a further aspect, the output product can be neutralized in a neutralization unit to stop the acid-catalyzed reaction from the cleavage reactor. In one aspect, the output product can be neutralized using a neutralizing agent, such as sodium phenate.

E. Purification System

The system may further comprise a purification reactor that is configured to receive a material (e.g., the output product of the cleavage reactor) and to purify the one or more of phenol, acetone, and alpha-methylstyrene to produce a purified output product. The purified output material may optionally be fed to a condensation reactor that is configured to receive the purified output product and to produce one or more of Bisphenol A and paracumylphenol.

F. Condensation Reactor

An optional condensation reactor (or BPA production reactor 208) may be configured to receive the output product and/or purified output product and to produce one or more of Bisphenol A and para-cumylphenol.

Instrumentation

In an aspect, the system can be configured to measure quantitative values and to assess conditions of the reaction stream. In a further aspect, the second fluid loop 104 can comprise an instrument (e.g., instrument 110) configured to measure characteristics of a fluid flowing through the second fluid loop 104. In an aspect, the instrument can be configured to measure water percentage. In another aspect, the instrument can be configured to measure conductivity. In yet a further aspect, the instrument can be configured to measure flow rate. In an aspect, the instrument can be configured to measure spectral characteristics. Spectral composition obtained can correlate to a chemical composition in the loop, i.e. concentrations for various components can be obtained (e.g., phenol, acetone, cumene, DCP, CHP, AP, etc.)

Near-infrared is a widely used analytical measurement tool in chemical, pharmaceutical, petroleum, and agricultural industries. The technique requires little or no sample preparation and is nondestructive, reagent-less, simple and fast. In addition, near-infrared (NIR) spectroscopy exhibits the capability to extract quantitative information of several species within a sample from a measured spectrum thereby making this approach ideal for multicomponent determination of complex matrixes. In an aspect, the instrument can comprise a NIR spectroscopy device. In an aspect, the system can comprise an NIR probe.

Method

The disclosure concerns methods of cumene hydroperoxide cleavage with an online instrumentation configuration. Certain methods can relate to measuring the characteristics of a flow through instrumentation line. One method can comprise causing fluid to flow through a first stage comprising one or more reactors and a fluid pump configured in fluid communication with each other. The first stage can be configured to decompose a cumene hydroperoxide in the presence of a catalyst mixture to form a dicumyl peroxide mixture. At least a portion of that fluid can be caused to flow through an instrumentation line in open fluid communication with the first stage. The instrumentation line can comprise an instrument configured to measure one or more characteristics of at least a portion of the fluid flowing through the instrumentation line. The input of the instrument can be disposed downstream of the fluid pump.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

ASPECTS

The disclosed systems and methods include at least the following aspects.

Aspect 1: A system comprising: a first fluid loop comprising one or more reactors and a fluid pump configured in fluid communication with each other, wherein the fluid pump is configured to cause an output of the one or more reactors to flow as an input to the one or more reactors; and a second fluid loop in fluid communication with the first fluid loop, the second fluid loop comprising an instrument configured to measure a characteristic of a fluid flowing through the second loop, wherein an input of the second fluid loop is disposed downstream of the fluid pump and an output of the second fluid loop is disposed upstream of the fluid pump.

Aspect 2: The system of aspect 1, wherein the one or more reactors of the first fluid loop comprise tubing, a pre-heater, a heat exchanger, a calorimeter, or any combination thereof.

Aspect 3: The system of any of aspects 1-2, wherein the first fluid loop is configured to react cumene hydroperoxide with dimethyl benzyl alcohol to form dicumyl peroxide.

Aspect 4: The system of any of aspects 1-3, further comprising a storage vessel in fluid communication with the output of the one or more reactors to receive a fluid therefrom.

Aspect 5: The system of any of aspects 1-4, further comprising a second stage including one or more second reactors in fluid communication with the output of the one or more reactors of the first fluid loop.

Aspect 6: The system of aspect 5, wherein the second stage is configured to form a phenol, acetone, and AMS mixture from decomposition of a dicumyl peroxide mixture.

Aspect 7: The system of aspect 6, wherein the dicumyl peroxide mixture is received from the first fluid loop.

Aspect 8: The system of any of aspects 1-7, wherein the instrument is configured to measure one or more of a water percentage, conductivity, spectral characteristics, and flow rate.

Aspect 9: The system of any of aspects 1-8, wherein the instrument comprises a near infrared spectroscopy device.

Aspect 10: The system of any of aspects 1-9, wherein the second fluid loop is in open fluid communication with the first fluid loop.

Aspect 11: A system comprising: a first stage comprising one or more reactors and a fluid pump configured in fluid communication with each other, wherein the fluid pump is configured to cause an output of the one or more reactors to flow as an input to the one or more reactors, and wherein the first stage is configured to decompose a cumene hydroperoxide in the presence of a catalyst mixture to form a dicumyl peroxide mixture; and a instrumentation line in open fluid communication with the first stage, the instrumentation line comprising an instrument configured to measure a characteristic of a fluid flowing through the instrumentation line, wherein an input of the instrumentation line is disposed downstream of the fluid pump.

Aspect 12: The system of aspect 11, wherein the one or more reactors of the first stage comprise tubing, a pre-heater, a heat exchanger, a calorimeter, or any combination thereof.

Aspect 13: The system of any of aspects 11-12, further comprising a second stage including one or more second reactors in fluid communication with the output of the one or more reactors of the first stage.

Aspect 14: The system of aspect 13, wherein the second stage is configured to form a phenol, acetone, and AMS mixture from decomposition of the dicumyl peroxide mixture received from the first stage.

Aspect 15: The system of any of aspects 11-14, wherein the instrument is configured to measure one or more of a water percentage, conductivity, spectral characteristics, and flow rate.

Aspect 16: The system of any of aspects 11-15, wherein the instrument comprises a near infrared spectroscopy device.

Aspect 17: A method comprising: causing fluid to flow within a first stage comprising one or more reactors and a fluid pump configured in fluid communication with each other, wherein the first stage is configured to decompose a cumene hydroperoxide in the presence of a catalyst mixture to form a dicumyl peroxide mixture; and causing at least a portion of the fluid to flow through a instrumentation line in open fluid communication with the first stage, the instrumentation line comprising an instrument configured to measure a characteristic of the at least a portion of the fluid flowing through the instrumentation line, wherein an input of the instrument line is disposed downstream of the fluid pump.

Aspect 18: The method of aspect 17, wherein the one or more reactors comprise tubing, a pre-heater, a heat exchanger, a calorimeter, or any combination thereof.

Aspect 19: The method of any of aspects 17-18, wherein the instrument is configured to measure one or more of a water percentage, conductivity, spectral characteristics, and flow rate.

Aspect 20: The method of any of aspects 17-19, wherein the instrument comprises a near infrared spectroscopy device.

EXAMPLES

Detailed embodiments of the present disclosure are disclosed herein; it is to be understood that the disclosed embodiments are merely exemplary of the disclosure that may be embodied in various forms. Therefore, specific structural and functional details disclosed herein are not to be interpreted as limits, but merely as a basis for teaching one skilled in the art to employ the present disclosure. The specific examples below will enable the disclosure to be better understood. However, they are given merely by way of guidance and do not imply any limitation.

As illustrated in FIG. 1, an open fluid communication can be provided for online measurements of a fluid loop. Such a configuration can maintain necessary fluid flow for instrumentations. Further, the open fluid communication can eliminate valve failure by removing the need for a valve to control flow from a first fluid loop to instrumentation. As such, overall equipment can be simplified, piping length can be minimized, control logic code can be simplified, and improved measurements of multiple variables can be realized in start-up/shut-down or normal operation. Choice of instruments (conductivity, NIR) allows measurement of composition, water content, etc. without the need for filters. As an example, by performing CHP cleavage in a system incorporating open fluid communication and NIR analytical instrumentation, one can achieve improved cleavage as well as improved data collection. Online instrumentation such as a flow meter can be used with the systems of the present disclosure. Accordingly, overall safety can be improved since confidence in flow measurement from an online flow meter is improved. A conductivity meter can be used to provide data that is proportional to the acid concentration in the first fluid loop under normal operation. Such conductivity meter can also indicate upset conditions when there is a salt break through from CHP concentration. Furthermore, the use of an NIR probe allows percent water and composition (e.g., organic composition) to be measured without the need for industry standard online water measurement devices (which require filters). By removing the conventional filters, plugging problems are reduced/eliminated.

It will be apparent to those skilled in the art that various modifications and variations can be made in the present disclosure without departing from the scope or spirit of the disclosure. Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A system comprising:
   a first fluid loop comprising one or more reactors and a fluid pump configured in fluid communication with each other, wherein the fluid pump is configured to cause an output of the one or more reactors to flow as an input to the one or more reactors; and
   a second fluid loop in fluid communication with the first fluid loop, the second fluid loop comprising an instrument configured to measure a characteristic of a fluid flowing through the second loop, wherein an input of the second fluid loop is disposed downstream of the fluid pump and an output of the second fluid loop is disposed upstream of the fluid pump;
   further comprising a second stage including one or more second reactors in fluid communication with the output of the one or more reactors of the first fluid loop.

2. The system of claim 1, wherein the one or more reactors of the first fluid loop comprise tubing, a pre-heater, a heat exchanger, a calorimeter, or any combination thereof.

3. The system of claim 1, wherein the first fluid loop is configured to react cumene hydroperoxide with dimethyl benzyl alcohol to form dicumyl peroxide.

4. The system of claim 1, further comprising a storage vessel in fluid communication with the output of the one or more reactors to receive a fluid there from.

5. The system of claim 1, wherein the second stage is configured to form a phenol, acetone, and alpha-methylstyrene mixture from decomposition of a dicumyl peroxide mixture.

6. The system of claim 5, wherein the dicumyl peroxide mixture is received from the first fluid loop.

7. The system of claim 1, wherein the instrument is configured to measure one or more of a water percentage, conductivity, spectral characteristics, and flow rate.

8. The system of claim 1, wherein the instrument comprises a near infrared spectroscopy device.

9. The system of claim 1, wherein the second fluid loop is in open fluid communication with the first fluid loop.

10. A system comprising:
    a first stage comprising one or more reactors and a fluid pump configured in fluid communication with each other, wherein the fluid pump is configured to cause an output of the one or more reactors to flow as an input to the one or more reactors, and wherein the first stage is configured to decompose a cumene hydroperoxide in the presence of a catalyst mixture to form a dicumyl peroxide mixture; and
    an instrumentation line in open fluid communication with the first stage, the instrumentation line comprising an instrument configured to measure a characteristic of a fluid flowing through the instrumentation line, wherein an input of the instrumentation line is disposed downstream of the fluid pump;
    further comprising a second stage including one or more second reactors in fluid communication with the output of the one or more reactors of the first stage.

11. The system of claim 10, wherein the one or more reactors of the first stage comprise tubing, a pre-heater, a heat exchanger, a calorimeter, or any combination thereof.

12. The system of claim 11, wherein the second stage is configured to form a phenol, acetone, and alpha-methylstyrene mixture from decomposition of the dicumyl peroxide mixture received from the first stage.

13. The system of claim 1, wherein the instrument is configured to measure one or more of a water percentage, conductivity, spectral characteristics, and flow rate.

14. The system of claim 1, wherein the instrument comprises a near infrared spectroscopy device.

15. A method comprising:
    causing fluid to flow within a first stage comprising one or more reactors and a fluid pump configured in fluid communication with each other, wherein the first stage is configured to decompose a cumene hydroperoxide in the presence of a catalyst mixture to form a dicumyl peroxide mixture; and causing at least a portion of the fluid to flow through a instrumentation line in open fluid communication with the first stage, the instrumentation line comprising an instrument configured to measure a characteristic of the at least a portion of the fluid flowing through the instrumentation line, wherein an input of the instrumentation line is disposed downstream of the fluid pump;

wherein the instrument is configured to measure one or more of a water percentage, conductivity, spectral characteristics, and flow rate.

16. The method of claim 15, wherein the one or more reactors comprise tubing, a pre-heater, a heat exchanger, a calorimeter, or any combination thereof.

17. The method of claim 1, wherein the instrument comprises a near infrared spectroscopy device.

* * * * *